United States Patent
Callens et al.

(10) Patent No.: US 10,174,075 B2
(45) Date of Patent: Jan. 8, 2019

(54) USE OF A TETRAPHENYLBORATE (TPB) SALT FOR THE SEPARATION OF BIOMOLECULES

(71) Applicant: CORDEN PHARMA BRUSSELS PC, Brussels (BE)

(72) Inventors: Roland Callens, Grimbergen (BE); Laurent Jeannin, Jette (BE)

(73) Assignee: CORDEN PHARMA BRUSSELS PC, Brussels (BE)

( * ) Notice: Subject to any disclaimer, the term of this patent is extended or adjusted under 35 U.S.C. 154(b) by 0 days.

(21) Appl. No.: 15/451,020

(22) Filed: Mar. 6, 2017

(65) Prior Publication Data

US 2017/0183375 A1 Jun. 29, 2017

Related U.S. Application Data

(63) Continuation of application No. 12/999,033, filed as application No. PCT/EP2009/057548 on Jun. 17, 2009, now Pat. No. 9,611,291.

(30) Foreign Application Priority Data

Jun. 17, 2008 (WO) ............... PCT/EP2008/057637

(51) Int. Cl.
| | | |
|---|---|---|
| C07K 7/08 | (2006.01) | |
| C07K 1/06 | (2006.01) | |
| C12N 15/10 | (2006.01) | |
| C07K 1/00 | (2006.01) | |
| C07K 1/14 | (2006.01) | |
| C07K 1/30 | (2006.01) | |
| C07K 5/09 | (2006.01) | |
| C07K 5/097 | (2006.01) | |
| C07K 14/47 | (2006.01) | |
| C07K 7/06 | (2006.01) | |

(52) U.S. Cl.
CPC ............ *C07K 1/303* (2013.01); *C07K 5/0817* (2013.01); *C07K 5/0821* (2013.01); *C07K 7/06* (2013.01); *C07K 14/4723* (2013.01)

(58) Field of Classification Search
None
See application file for complete search history.

(56) References Cited

U.S. PATENT DOCUMENTS

| | | | |
|---|---|---|---|
| 4,923,966 A | 5/1990 | Callens et al. | |
| 4,954,616 A | 9/1990 | Callens et al. | |

FOREIGN PATENT DOCUMENTS

| | | |
|---|---|---|
| JP | 64-16791 A | 1/1989 |
| JP | 64-16792 A | 1/1989 |
| JP | 2004-514644 A | 5/2004 |
| WO | 01/66147 A2 | 9/2001 |

OTHER PUBLICATIONS

Tezuka et al., "Epidermal structural proteins: I. isolation and purification of keratohyalin granules of the newborn rat," Biochim. Biophys. Acta 261:402-417 (1972).*
Gran, "Isolation of oxytocic peptides from Oldenlandia affinis by solvent extraction of tetraphenylborate complexes and chromatography on sepandex LH-20", Lloydia, 36:207-208 (1973).*

* cited by examiner

*Primary Examiner* — Julie Ha
*Assistant Examiner* — Kristina M Hellman
(74) *Attorney, Agent, or Firm* — Duane Morris LLP; J. Rodman Steele, Jr.; Gregory M. Lefkowitz

(57) ABSTRACT

Process for the separation of a biomolecule containing at least one cationic group from a liquid medium containing the biomolecule, which includes the use of a tetraphenylborate (TPB) salt.

11 Claims, No Drawings
Specification includes a Sequence Listing.

USE OF A TETRAPHENYLBORATE (TPB) SALT FOR THE SEPARATION OF BIOMOLECULES

CROSS-REFERENCE TO RELATED APPLICATIONS

This application is a continuation of U.S. patent application Ser. No. 12/999,033, filed on Dec. 14, 2010, which is a U.S. national stage application under 35 U.S.C. § 371 of International Application No. PCT/EP2009/057548 filed on Jun. 17, 2009, which claims priority to International Application No. PCT/EP2008/057637 filed on Jun. 17, 2008, which are incorporated herein by reference in their entirety to the full extent permitted by law.

The present invention relates to a process for the separation of a biomolecule containing at least one cationic group and to a process for the manufacture of a biomolecule involving this use.

The process of the present invention can for instance be used for the manufacture of Eptifibatide (SEQ ID NO: 5) that selectively blocks the platelet glycoprotein IIb/IIIa receptor. It reversibly binds to platelets and has a short half-life. It has demonstrated efficacy as an intravenous solution in the treatment of patients during coronary angioplasty, myocardial infarction and angina.

The process of the present invention can also be used for the manufacture of Omiganan. Omiganan is the Common international Denomination (CTD) for the peptide H-Ile-Leu-Arg-Trp-Pro-Trp-Trp-Pro-Trp-Arg-Arg-Lys-NH2 (SEQ ID NO 1) that is mostly used in the form of its pentahydrochloride (5 HCl) salt. Omiganan is a cationic antimicrobial peptide. Recent research has also shown that it may play a role in the inflammatory response. Omiganan, in in vitro assay, demonstrated a rapid bactericidal activity against micro-organisms that colonize the skin and that may play a role in the pathogenesis of inflammatory diseases.

U.S. Pat. No. 5,262,567 discloses the use of a compound including a guanidine group and an unsubstituted tetraphenylborate ion as intermediate in the synthesis of peptides. As an example, the synthesis of the compound formed by arginine and tetraphenylborate (TPB) and its use in the synthesis of the peptide Boc-Leu-Arg-OH has been described.

It has now been found, surprisingly, that an improved separation of a biomolecule from a liquid medium, in particular a biomolecule containing at least one cationic group by the use of a tetraphenylborate (TPB) salt enables the desired biomolecule to be obtained in high yield and with high purity.

The invention thus relates to a process for the separation of a biomolecule containing at least one cationic group from a liquid medium containing said biomolecule, which comprises the use of a tetraphenylborate (TPB) salt.

For the purpose of the present invention, the term "the cationic group" refers to a functional group of the biomolecule having a positive charge. The cationic groups in this invention are often selected from a guanidine group or an amino group. When the cationic group is an amino group, it is often selected from protonated primary, secondary and, preferably, tertiary amino groups. More preferably, the amino group is a quarternary (ammonium) group, for example a tetraalkylammonium group. A guadinine group is another preferred cationic group.

For the purpose of the present invention, the term "TPB" denotes tetraphenylborate. The TPB anion can be substituted on the benzene rings or it can be unsubstituted. Preferably, the TPB anion is unsubstituted.

Examples of suitable substituted TPB anions include, for example, the tetrakis[3,5-bis(trifluoromethylphenyl]borate.

In the present invention, the TPB salt used is generally capable of forming an aqueous solution. The cation in the TPB salt is often an inorganic cation. Suitable inorganic ions are for example the sodium (Na+) and lithium (Li+). Preferred are LiTPB and NaTPB. The most preferably used tetraphenylborate salt is NaTPB.

In the process according to the invention, the quantity of tetraphenylborate salt used is generally from 1 to 10 equivalents of tetraphenylborate salt per cationic group present in the biomolecule, preferably this quantity is from 1 to 2 equivalents, more preferably from 1 to 1.1 equivalents.

In the process according to the invention, the TBP salt is preferably used together with an alkaline agent. The alkaline agent may be selected in particular from inorganic bases, for instance $NaHCO_3$ and $Na_2CO_3$. In general, the selection of the alkaline agent will depend on the sensitivity of the biomolecule to be purified towards alkaline conditions.

For the purpose of the present invention, the term "biomolecule-TPB salt" refers to biomolecule tetraphenylborate (TPB) salt.

For the purpose of the present invention, "a liquid medium containing the biomolecule" is understood to denote in particular a solution of the biomolecule in a solvent selected from an aqueous solvent ("aqueous solution"), an organic solvent ("organic solution") or mixtures thereof.

For the purpose of the present invention, the term "aqueous solvent" refers on particular to water and solutions in water of water soluble compounds, for example salt water or any other aqueous mineral salt solution.

"Compound not miscible with water" is understood to denote in particular a compound which when contacted with an aqueous solution allows separate an aqueous phase from an organic phase by decantation.

In the present invention, the biomolecule is generally selected from the group consisting of a peptide, a peptide derivative, an oligonucleotide an oligonucleotide derivative and a polysaccharide.

For the purpose of the present invention, the term "peptide" refers to a polymer in which the monomers are amino acids covalently attached together through amide bonds. Peptides are two or often more amino acids monomers long. In addition, all specific peptide sequences herein are represented by formulae whose left to right orientation is in the conventional direction of amino-terminus to carboxy-terminus.

For the purpose of the present invention, the term "amino acid" is intended to denote any compound comprising at least one $NR_1R_2$ group, preferably $NH_2$ group, and at least one carboxyl group. The amino acids of this invention can be naturally occurring or synthetic. The natural amino acids, with exception of glycine, contain a chiral carbon atom. Unless otherwise specifically indicated, the compounds containing natural amino acids with the L-configuration are preferred. Amino acid residues are abbreviated as follows throughout the application: Arginine is Arg or R; Lysine is Lys or K; Proline is Pro or P; Tryptophane is Tip or W; Aspartic acid is Asp or D; Cysteine is Cys or C.

For the purpose of the present invention, the term "carboxy-terminus" of a peptide is the end of an amino acid sequence terminated by a free carboxyl group (—COOH). On the other hand, the term "amino-terminus" of a peptide refers to the end of an amino acid sequence terminated by an amino acid with a free amino group (—NH$_2$).

As used herein, the term "peptide derivative" includes an analog in which one or more amino acid residues have been replaced by the corresponding D-isomer or by a non-natural amino acid residue, or a chemical derivative thereof. A chemical derivative of a peptide includes, but is not limited to, a derivative containing additionally at least 1 chemical moiety not normally part of a peptide. Examples of such derivatives are: (a) N-acyl derivatives of the amino terminal or of another free amino group, wherein the acyl group may be either an alkanoyl group such as acetyl, hexanoyl, octanoyl; an aroyl group, e.g., benzoyl, or biotinyl; (b) esters of the terminal carboxyl group or of another free carboxyl or hydroxy groups; and (c) amides of the terminal carboxyl group or of another free carboxyl groups produced by reaction with ammonia or with a suitable amine.

The term "oligonucleotide", in the frame of the present invention, denotes in particular an oligomer of nucleoside monomeric units comprising sugar units connected to nucleobases, said nucleoside monomeric units being connected by internucleotide bonds. An "internucleotide bond" refers in particular to a chemical linkage between two nucleoside moieties, such as the phosphodiester linkage typically present in nucleic acids found in nature, or other linkages typically present in synthetic nucleic acids and nucleic acid analogues. Such internucleotide bond may for example include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group. Typical internucleotide bonds are diesters of phosphoric acid or its derivatives, for example phosphates, thiophosphates, dithiophosphates, phosphoramidates and thiophosphoramidates. In the present invention, the internucleotide bonds are generally protected by a suitable protective group. A β-cyanoethyl Group is an example of a suitable protective group.

The term "nucleoside" is understood to denote in particular a compound consisting of a nucleobase connected to a sugar. Sugars include, but are not limited to, furanose rings such as ribose and 2'-deoxyribose and non-furanose rings such as cyclohexenyl, anhydrohexitol and morpholino. The modifications, substitutions and positions indicated hereinafter of the sugar included in the nucleoside are discussed with reference to a furanose ring, but the same modifications and positions also apply to analogous positions of other sugar rings. The sugar may be additionally modified. As non limiting examples of the modifications of the sugar mention can be notably made of modifications at e.g. the 2'- or 3'-position, in particular the 2'-position of a furanosyl sugar ring including for instance hydrogen; hydroxy; alkoxy such as methoxy, ethoxy, allyloxy, isopropoxy, butoxy, isobutoxy, methoxyethyl, alkoxy, phenoxy; azido; amino; alkylamino; fluoro; chloro and bromo; 2'-4'- and 3'-4'-linked furanosyl sugar ring modifications, modifications in the furanosyl sugar ring including for instance substitutions for the ring 4'-O by S, CH$_2$, NR, CHF or CF$_2$.

The term "nucleobase" is understood to denote in particular a nitrogen-containing heterocyclic moiety capable of pairing with a, in particular complementary, nucleobase or nucleobase analog. Typical nucleobases are the naturally occurring nucleobases including the purine bases adenine (A) and guanine (G), and the pyrimidine bases thymine (T), cytosine (C) and uracil (U), and modified nucleobases including other synthetic and naturally nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halour-acil and -cytosine, 5-propynyl-uracil and -cytosine and other alkynyl derivatives of pyrimidine bases, 6-aza-uracil, -cytosine and -thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, and fluorinated bases. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Other potentially suitable bases include universal bases, hydrophobic bases, promiscuous bases and size-expanded bases.

For the purpose of the present invention, the term "oligonucleotide derivative" refers to a class of molecules such as 'peptide nucleic acids" (PNAs), morpholino phosphorodiamidate, peptide-oligonucleotide conjugates. The process according to the invention can suitably be applied to cationic PNAs.

Another class of biomolecules to which the process according to the invention can be applied is cationic polysaccharides such as cationic cellulose or cationic starch or cationic cyclodextrines. Cationic polysaccharides are for example polysaccharides functionalized with at least one cationic amino group as described above, in particular functionalized with at least one quarternary (ammonium) group.

Typical examples of peptides containing a guanidine group or an amino group are peptides which contain at least one amino acid selected from arginine, homoarginine and lysine. Peptides which contain at least one amino acid selected from arginine, and homoarginine are preferred.

Typical examples of oligonucleotides containing a guanidine group or an amino group are oligonucleotides which contain at least one nucleoside selected from adenosine, guanosine and cytosine and their derivatives thereof as listed above.

The process according to the present invention generally comprises the addition of a TPB salt to a liquid medium containing the biomolecule. The TPB salt can be supplied in solid form, or preferably as a solution, for example an aqueous solution. Addition of TPB salt to the liquid medium containing the biomolecule generally results in formation of a biomolecule TPB salt.

In the process according to the invention the number of cationic groups in the biomolecule is at least 1. Particular examples of biomolecules which can be separated according to the process according to the invention contain from 2 to 20, often from 3 to 15 cationic groups.

In the process according to the invention, the biomolecule separated from the liquid medium is generally obtained in the form of a solid biomolecule TPB salt or in the form of an organic solution suitable for use in a further reaction step.

When a solid biomolecule TPB salt is desired, the process according to the invention generally comprises precipitating or crystallizing the solid biomolecule TPB salt from a liquid medium containing the biomolecule. In this case, the liquid phase can be suitably contacted with an aqueous solution. Such aqueous solution may be, for example, water, salt water or any other aqueous mineral salt solution. In this case it is particularly advantageous to control the pH of the aqueous solution. The pH value of the aqueous solution is preferably controlled to be less than or equal to 10 more preferably, less than or equal to 9, still more preferably, less than or equal to 7.5. The pH value of the aqueous solution is preferably controlled to be higher than or equal to 5, more preferably, higher than or equal to 6.0, most preferably, higher than or equal to 6.5. The pH value of the aqueous solution may be controlled by the addition of mineral salts. Suitable salts which can be used include alkali or earth alkali chlorides, in particular sodium chloride, alkali or earth alkali sulphates, in particular potassium sulphate, alkali or earth alkali hydrogen carbonates, in particular sodium hydrogen carbonate. Particular preferred are salt water solutions including sodium chloride, preferably in an amount of 5% by weight of the salt water solution.

The precipitation or crystallization is generally carried out at a temperature from 0° C. to 20° C., preferably from 0° C. to 5° C.

The precipitated or crystallized biomolecule-TPB salt can be separated from the aqueous solution for example by filtration, decantation, centrifugation or spray drying.

According to one suitable approach, the biomolecule-TPB salt is collected via filtering and optionally washed. The biomolecule-TPB salt is preferably dried before optionally being submitted to further processing steps such as further reaction steps, lyophilisation, packaging and/or storage.

The invention will now be further explained with regard to specific embodiments.

In a first specific embodiment of the present invention, the liquid medium is an aqueous solution.

In this first aspect of the present invention, the aqueous solution of the biomolecule containing at least one cationic group can be obtained, for example, by adding an aqueous solution to the synthesis solution for the manufacture of said biomolecule in an organic solvent or solvent mixture.

Said aqueous solution containing the biomolecule containing at least one cationic group is then generally washed with an organic washing solvent. The organic washing solvent is preferably chosen from compounds which are not miscible with water. Non limiting examples of suitable organic washing solvents are selected from halocarbons such as dichloromethane (DCM) and chloroform, esters such as ethyl acetate (AcOEt) and isopropyl acetate (AcOiPr) and ethers such as diethyl ether, diisopropyl ether and methyl-tert.butylether (MTBE).

The optional washing step allows removing together with the organic phase organic reaction solvents used in the reaction medium, for example N,N-dimethylacetamide (DMA), N,N-dimethylformamide (DMF), N-methylpyrrolidone (NMP), reactants and/or starting reagents.

In a first aspect of the first embodiment of the present invention, the biomolecule containing at least one cationic group present in the aqueous solution is precipitated or crystallized, as described above, from the aqueous solution as a solid biomolecule tetraphenylborate (TPB) salt [biomolecule-TPB salt]. The precipitation or crystallisation can be realized, for example, by pouring the aqueous solution containing said biomolecule into an aqueous solution containing the TPB salt. In another example, an aqueous solution containing the TPB salt is added to the aqueous solution containing the biomolecule. The precipitated or crystallised biomolecule TPB salt can be further processed, as described above.

In a second aspect of the first embodiment of the process according to the invention, the biomolecule containing at least one cationic group present in the aqueous solution is extracted as a biomolecule-TPB salt into a first organic solution. The extraction is in general performed by contacting the aqueous solution with the TPB salt and a suitable organic solvent or solvent mixture. Preferred organic solvents are selected from halocarbons such as dichloromethane (DCM) and chloroform, esters such as ethyl acetate (AcOEt) and isopropyl acetate (AcOiPr) and ethers such as, diethyl ether, diisopropyl ether and MTBE, alone or in combination with alcohols such as for example n-butanol, iso-butanol and sec-butanol. Good results are obtained using dichloromethane.

In this aspect of the first embodiment of the process according to the invention, it is particularly advantageous to control the pH of the aqueous solution containing the biomolecule. The pH value of this aqueous solution is preferably controlled to be less than or equal to 10; more preferably, less than or equal to 9, still more preferably, less than or equal to 7.5. The pH value of this aqueous solution is preferably controlled to be higher than or equal to 5, more preferably, higher than or equal to 6.0, most preferably, higher than or equal to 6.5. The pH value of this aqueous solution may be controlled, for example, by the addition of an aqueous mineral salt solution. Suitable salts to be used in the above mentioned salt water solutions include alkali or earth alkali chlorides, in particular sodium chloride, alkali or earth alkali sulphates, in particular potassium sulphate, alkali or earth alkali hydrogen carbonates, in particular sodium hydrogen carbonate.

In a third aspect of the first embodiment of the process according to the invention, the invention relates to a process for the manufacture of a biomolecule-TPB salt containing at least one cationic group which comprises
(a) providing an aqueous solution of the biomolecule containing at least one cationic group
(b) adding a TPB salt to the aqueous solution
(c) recovering the biomolecule-TPB salt from the aqueous solution.

In a second embodiment of the process according to the invention, the liquid medium is an organic solution.

In this second aspect, the liquid medium is an organic solution to which after optional washing with an aqueous solution, the tetraphenylborate salt is added thereby providing a first organic solution containing the biomolecule-TPB salt. The organic solution of the biomolecule containing at least one cationic group can be obtained, for example, by diluting a synthesis solution for the manufacture of a biomolecule in an organic solvent or solvent mixture, in particular a reaction solvent as described above, after the completion of a synthesis step with an organic dilution solvent. The organic dilution solvent is preferably chosen from compounds which are not miscible with water. Preferably, organic dilution solvents are selected from halocarbons such as dichloromethane (DCM) and chloroform, esters such as ethyl acetate (AcOEt) and isopropyl acetate (AcOiPr) and ethers such as diethyl ether, diisopropyl ether and MTBE, alone or in combination with alcohols such as for example n-butanol, iso-butanol, sec-butanol. Good results are obtained using dichloromethane.

Said organic solution of the biomolecule containing at least one cationic group can be optionally washed with an aqueous solution, as described above, and further washed with an aqueous solution containing a TPB salt thereby providing a first organic solution in which the biomolecule remains dissolved as a biomolecule-TPB salt. The different washing steps allow to reduce impurities and other unwanted compounds content in the first organic solution.

In a first advantageous aspect of the second embodiment of process according to the invention, the first organic solution obtained is subjected to a further reaction step without isolation of the biomolecule-TPB salt.

A second advantageous aspect of the second embodiment of process according to the invention relates to a process for the manufacture of a biomolecule-TPB salt containing at least one cationic group comprises the following steps
  (a) providing an organic solution of the biomolecule containing at least one cationic group
  (b) adding a TPB salt to the organic solution
  (c) recovering the biomolecule-TPB salt from the first organic solution.

In a third embodiment of the process according to the invention, the first organic solution containing the biomolecule-TPB salt which can be obtained, for example, as described in the first and second embodiment above, can be treated with a further organic solvent or solvent mixture to obtain a second organic solution containing the biomolecule-TPB salt. The further organic solvent or solvent mixture may be added directly to the first organic solution containing the biomolecule-TPB salt or may be added after optional further treatment of said first organic solution. In this latter case which is preferred, the first organic solution containing the biomolecule-TPB salt may for example be concentrated, in particular by evaporation under vacuum, before the addition of the further organic solvent or solvent mixture. The further organic solvent preferably comprises at least one component selected from alcohols such as, preferably, methanol or methoxyethanol, amide type solvents such as N,N-dimethylacetamide (DMA), N,N-dimethylformamide (DMF), N-methylpyrrolidone (NMP), dimethylsulfoxide (DMSO), halocarbons such as dichloromethane (DCM) and chloroform, esters such as ethyl acetate (AcOEt) and isopropyl acetate (AcOiPr) and ethers such as diethyl ether, diisopropyl ether, dioxane, tetrahydrofuran (THF) and MTBE; pyridine, acetonitrile, or mixtures thereof. More preferably, the further organic solvent is selected from methanol, methoxyethanol, N,N-dimethylacetamide (DMA), N-methylpyrrolidone (NMP) and N,N-dimethylformamide (DMF). Good results are obtained with methanol or methoxyethanol.

In a first advantageous aspect of the third embodiment of the process according to the invention, the second organic solution obtained is subjected to a further reaction step without isolation of the biomolecule-TPB salt.

In a second advantageous aspect of the third embodiment of the process according to the invention, the biomolecule-TPB salt is separated from the second organic solution as a solid biomolecule-TPB salt by precipitation or crystallisation, as described above. The precipitation or crystallisation can be performed by the addition of the second organic solution containing the biomolecule-TPB salt to an aqueous solution. Alternatively, the precipitation or crystallisation can also be performed by the addition of an aqueous solution to said second organic solution. The precipitated or crystallised biomolecule TPB salt can be further processed as described above.

In a third advantageous aspect of the third embodiment of the process according to the invention, the second organic solution containing the biomolecule-TPB salt is further subjected to a concentrating step. The concentrating step is often carried out by evaporation under vacuum.

In a fourth embodiment of the process according to the invention, the first organic solution containing the biomolecule-TPB salt, which can be obtained, for example, as described in the first or second embodiment above, is subjected to a concentrating step, for example as described here before, to provide a concentrated organic solution containing the biomolecule-TPB salt.

The biomolecule-TPB salt may be separated from the concentrated organic solution, which can be obtained as described in the third and fourth embodiments, for example, by precipitation or crystallisation, as described above. The precipitation or crystallisation can be performed by pouring the concentrated organic solution containing the biomolecule-TPB salt into an aqueous solution. Alternatively, the precipitation or crystallisation can also be performed by the addition of an aqueous solution to said concentrated organic solution. The precipitated or crystallised biomolecule TPB salt can be further processed as described above.

The resulting concentrated organic solution containing the biomolecule-TPB salt can be used directly for a further reaction step. Optionally, said concentrated organic solution can be diluted with a further organic solvent as described here before and then subjected to a further reaction step.

The different embodiments of the process according to the invention can preferably be applied to a biomolecule which is selected from the group consisting of a peptide containing at least one cationic group or a derivative thereof, more particularly, peptide or peptide derivative containing a guanidine group or an amino group. Typical examples of peptides or peptide derivatives containing a guanidine group or an amino group are peptides which contain at least one amino acid selected from arginine (Arg), homoarginine (homo Arg) and lysine (Lys).

The invention thus relates in another specific aspect to a process for the manufacture of a peptide or a derivative thereof comprising one or more amino acid units containing a cationic group, comprising the steps
  (a) coupling in an organic solution a first amino acid or a first peptide with a second amino acid or second peptide, wherein the first and/or the second amino acid or peptide contains a cationic group, to produce a peptide containing a cationic group.
  (b) adding a TPB salt after the completion of the coupling step; and
  (c) separating as described herein before the peptide containing a cationic group or the derivative thereof from an aqueous solution or an organic solution.

The process according to the invention is especially advantageous if the number of cationic groups in the peptide is from 2 to 20, preferably from 3 to 15.

The process of the present invention is especially beneficial when the coupling step involves a peptide containing the amino acid Arg or Har. It has been found surprisingly that the use of a protecting group for the side chain in Arg or Har can be omitted when a tetraphenylborate in steps (b) and (c). The peptide manufacturing process according to the invention can be advantageously applied to the manufacture of Omiganan (SEQ ID NO: 1) or Eptifibatide (SEQ ID NO: 5).

In step (a) of the peptide manufacturing process of the present invention, protecting groups can be used in general for one or more amino groups in the amino acids or peptide intermediates involved.

By way of illustration, the following protecting groups may be employed in the peptide manufacturing process of the invention: acyl-type protecting groups such as formyl, trifluoroacetyl, phthaloyl, 4-toluenesulfonyl, benzenesulfonyl and 2-nitrophenylsulfenyl, aromatic urethane-type protecting groups such as substituted or unsubstituted benzyloxycarbonyl (Z), p-bromobenzyloxycarbonyl, p-methoxybenzyloxycarbonyl, benzhydryloxycarbonyl, 2-(4-biphenylyl) prop-2-yl-oxycarbonyl, dimethyloxphenyl) prop-2-yl-oxycarbonyl, and triphenylphosphonoethyloxycarbonyl, aliphatic urethane-type protecting groups, in particular tert-butyloxycarbonyl (BOC), diisopropylmethoxycarbonyl, isopropyloxycarbonyl, ethoxycarbonyl, allyloxycarbonyl, 9-fluorenylmethyloxycarbonyl (Fmoc), 2-methylsulfonylethyloxycarbonyl and 2,2,3-trichloroethyloxycarbonyl, cycloalkyl urethane-type protecting groups such as cyclopentyloxycarbonyl, adamantyloxycarbonyl, cyclohexyloxycarbonyl, tert-amyloxycarbonyl and isobornyloxycarbonyl, thiourethane-type protecting groups, in particular phenylthiocarbonyl, alkyl-type protecting groups such as especially triphenylmethyl (trityl) and benzyl trialkylsilane groups such as, for example tert.butyl-dimethylsilyl and alkoxy groups such as for example methyl ester, ethyl ester, tert-butyl ester and benzyl ester and a p-nitrobenzylester.

In the peptide manufacturing process of the invention, the first amino acid or peptide has in general an activated carboxyl group. Various activating groups may be used in the process of the invention, for example groups derived from N,N-dicyclohexycarbodiimide (DCC), N-(3-dimethylaminopropyl)-N'-ethylcarbodiimide (EDC), pivaloyl chloride (PivCl), i-butylchloroformate (IBCF). In addition to these activating groups additives are sometimes used advantageously. Preferred additives are N-hydroxysuccinimide (Suc-OH), N-hydroxybenzotriazole (HOBt), or 3,4-dihydro-3-hydroxy-4-oxo-1,2,3 benzotriazine (HOOBt).

A further particular aspect of the peptide manufacturing process according to the invention is related to a process in which the aqueous or organic solution of a peptide containing at least one cationic group or derivative thereof is obtained by adding an aqueous solution to the synthesis solution for the manufacture of said peptide in an organic solvent after the completion of a coupling step.

In general, the synthesis solution after a peptide coupling step may or may not contain a base. In consequence, the subsequent steps may depend on whether or not a base is present.

In a first embodiment of the peptide manufacturing process according to the invention where no base is present in the synthesis solution, it is preferable to dilute the synthesis solution with an aqueous solution of an acid for example hydrochloric acid. A preferably, the solution is then washed with an organic solvent or mixtures thereof. The organic solvent is preferably chosen from compounds which are not miscible with water. Non limiting examples of such suitable organic solvents are selected from halocarbons such as dichloromethane (DCM) and chloroform; esters such as ethyl acetate (AcOEt) and isopropyl acetate (AcOiPr) and ethers such as diethyl ether, diisopropyl ether and MTBE. A number of different solvents may be used. Especially advantageous is the use of dichloromethane, ethyl acetate, isopropyl acetate, diisopropyl ether, and MTBE, alone or in combination. The washing step allows removing together with the organic phase organic solvents used in the reaction medium (for example DMF, DMA, NMP), reactants (for example HOBt, HOOBt) and/or starting amino acids or peptides.

In this embodiment of the present invention, the peptide containing at least one cationic group or derivative thereof is present in the aqueous solution and the addition of a TPB salt to the aqueous solution and the recovery of the tetraphenylborate (TPB) salt of the peptide or derivative thereof can be carried out according to the process according to the invention, as described above, in particular as described in the first embodiment of the process according to the invention.

In a second embodiment of the peptide manufacturing process according to the invention wherein a base is present in the synthesis solution, it is preferred to dilute a synthesis solution with a dilution solvent as described above. In a second step, the organic solution comprising organic solvents (organic phase) may be advantageously washed to the aqueous solution of an acid. This washing step may allow the elimination through the aqueous phase of starting compounds, especially when they contain Arg, as well as certain basic additives (for example TEA, DIPEA) and reactants (for example EDU) which might form a salt with TPB.

In this embodiment of the invention, the peptide containing at least one cationic group or derivative thereof is present in the organic solution and the addition of a TPB salt to the organic solution and the recovery of the tetraphenylborate (TPB) salt of the peptide a derivative thereof can be realized according to the process of the present invention, as described in the different embodiments above.

In one particular embodiment, which is particularly suitable in the framework of synthesis of Omiganan (SEQ ID NO: 1), the peptide synthesis process according to the invention comprises forming a tetraphenylborate salt of an Arg containing peptide. Typically said tetraphenylborate salt of an Arg containing peptide is formed by contacting a coupling step reaction medium containing an Arg containing peptide, which is usually obtained by a coupling step according to the process according to the invention with a source of tetraphenylborate anions. Tetraphenylborate salts are suitable as source of tetraphenylborate anions.

Hence, it is preferred to perform at least one step in the presence of a tetraphenylborate salt (TPB) which is preferably added after the completion of at least one coupling step.

The cation in the tetraphenylborate (TPB) salt can be inorganic or organic. Examples of organic ions are the tetraethylammonium, diisopropylethylammonium, N-ethylpiperidinium, N-methylmorpholinium, N-ethylmorpholinium. Suitable inorganic ions are for example the sodium ($Na^+$) or lithium ($Li^+$). Most preferably, a tetraphenylborate salt is used that is capable of forming an aqueous solution. Preferred are LiTPB and NaTPB. The most preferably used tetraphenylborate salt is NaTPB.

The TPB anion can be substituted on its benzene ring or it can be used without any substitution. Preferably, the TPB anion is not substituted. Examples of suitable substituted TPB anions include, for example, the tetrakis(3,5-bistrifluoromethylphenyl)borate.

The quantity of the tetraphenylborate salt employed may vary within wide limits. Preferably, from 1 to 10 equivalents, preferably 1 to 1.5 equivalents of tetraphenylborate salt is employed per Arg unit in the Arg containing peptide.

The tetraphenylborate salt is preferably employed in the process of the present invention during the work-up after the completion of at least one coupling step, in the presence of a solvent or a mixture of solvents. Suitable solvents are especially methanol, methoxyethanol, dichloromethane, n-butanol, iso-butanol, sec-butanol, and tert-butanol. Good results were obtained using methoxyethanol.

In this embodiment, said tetraphenylborate salt of an Arg containing peptide can advantageously be subjected without isolation to at least one further synthesis step. Often, said tetraphenylborate salt of an Arg containing peptide is subjected at least to a deprotection step followed by a coupling step.

The invention also relates to a solid biomolecule-TPB salt containing at least one cationic group. Peptides, in particular as herein described and more particularly Arg or Har containing peptides are preferred biomolecules in the solid biomolecule-TPB salt according to the invention may notably be obtained according to the process of the invention.

It has been found, surprisingly, that the solid biomolecule-TPB salt is substantially stable when stored.

"Substantially stable" is understood to denote in particular the fact that when comparing the biomolecule content of the biomolecule-TPB salt before and after storage, the biomolecule-TPB salt content found after storage is at least 98%, preferably at least 99% of the biomolecule content before storage.

The invention consequently also relates to a method of storing the solid biomolecule-TPB salt according to the invention The storage of the solid biomolecule-TPB salt is generally carried out at a temperature less than or equal to 25° C.; more preferably, less than or equal to 22° C., still more preferably, less than or equal to 20° C. The storage of the solid biomolecule-TPB salt is generally carried out at a temperature higher than or equal to −90° C., often higher than or equal to −80° C. Preferably, the storage is carried out at a temperature higher than or equal to −20° C., more preferably higher than or equal to 0° C.

It has been found that use of the solid biomolecule-TPB salt according to the invention allows for long storage with relatively low energy consumption The solid biomolecule-TPB salt according to the invention is often stored for a time period longer than 24 hours, for example longer than 1 week. Stability may be observed for periods of time as long as 1 year, or longer. Often the storage time period will not exceed 6 months.

The invention also relates to the use of solid biomolecule-TPB salts as source of intermediate in biomolecule synthesis. The use according to the invention applies preferably to peptide fragments to be used in a coupling, deprotection or purification step.

The invention relates also to a process for the manufacture of a salt of a biomolecule containing at least one cationic group which comprises (a) providing a solution of a TPB salt of the biomolecule (b) contacting said solution with a counter-ion salt, the cation of which forms a salt with tetraphenylborate which is less soluble in the solution than the TPB salt of the biomolecule, so as to exchange the tetraphenylborate anion against the counter-ion (c) optionally recovering the counter-ion salt of the biomolecule from the solution.

In one embodiment, the ion exchange may be realized by adding to the solution a counter-ion salt, the cation of which forms a salt with the tetraphenylborate ion. Generally, the cation and solvent is chosen such that upon contacting the solution with the counter-ion salt, the cation TPB salt will precipitate from the solution. Suitable counter-ion salts are generally selected from potassium salts, for example, potassium chloride and potassium acetate and, preferably quaternary ammonium salts, for example tetraalkyl ammonium acetate and ammonium chloride. A tetraalkyl ammonium chloride, such as benzyltrimethylammonium chloride gives good results. In this specific embodiment of the present invention, the biomolecule-TPB salt is generally dissolved in an organic solvent. The organic solvent is preferably chosen from alcohols such as methanol or ethanol. Methanol is the most preferred alcohol. A combination of a cation chosen from quaternary ammonium cations for example benzyltrimethylammonium cation and an alcohol is particularly preferred.

The molar ratio counter-ion salt/TPB anion used in this embodiment is generally about 1, preferably from 1 to 1.1.

In another embodiment, the ion exchange is carried out by using an ion exchange resin. In this embodiment the exchange is preferably performed by passing the biomolecule-TPB salt solution through a column containing the exchange resin. Suitable examples of exchange resins contain immobilized amino cationic groups as described above, in particular quaternary (ammonium), groups with the desired counter-ion, in particular acetate or chloride. A specific example of suitable ion exchange resin is commercialized by Rohm and Haas under the denomination IRA 958. The exchange resin can be optionally washed with an organic solvent preferably chosen from alcohols such as methanol, ethanol. Methanol is most preferred alcohol.

The following examples are intended to illustrate the invention without, however, limiting its scope.

The ratios indicated refer to volume ratios. If nothing else is indicated, the purity of the compound was more than 98% by weight and the ratios indicated refer to volume ratios. In cases where iso-butanol was used, sec-butanol could be used as well.

In these examples and throughout this specification the abbreviations employed are defined as follows: Boc is t-butoxycarbonyl, n-BuOH is n-butanol, DCM is dichloromethane, DIPEA is N,N-diisopropylethylamine, DMF is N,N-dimethylformamide, DMA is N,N-dimethylacetamide, Fmoc is fluorenylmethyloxycarbonyl, HBTU is N,N,N',N'-tetramethyl-O-(1H-benzotriazol-1-yl) uronium-hexafluororphosphate), HOBt is 1-hydroxybenzotriazole, HOOBT is 3,4-dihydro-3-hydroxy-4-oxo-1,2,3-benzotriazine, EDC is N,N-dimethylaminopropylcarbodiimide, DCC is dicyclohexyl carbodiimide, i-BuOH is iso-butanol, IPE is diisopropylether, McCN is acetonitrile, McOH is methanol, NMM is N-methylmorpholine, NMP is 1-methyl-2-pyrrolidone, THF is tetrahydrofuran, pNA is p-nitro anilinamide, Tos is tosyl, MTBE is methyl-tert-butylether.

EXAMPLE 1

Synthesis of HCLH-Arg-Lys(Boc)-NH$_2$ 1.02 equivalents of Z-Arg-OH.HCl (Mw=344.8) were added at room temperature to a mixture of DMA and CH$_2$Cl$_2$ (6/4). Thereafter, 1.03 equivalents of HOBt (N-Hydroxybenzotriazole, Mw=135.12) and 1.00 equivalent of H-Lys (Boc)-NH$_2$ (Mw=245.3; purity: 99%) were added. After cooling the solution to 0±5° C., 1.03 equivalents of EDC.HCl(Mw 191.7) were added.

Stirring was continued for further 30 min at 0±5° C. and then for at least 2 hours at room temperature. After checking for the completion of the reaction by HPLC, the reaction mixture was diluted with a CH$_2$Cl$_2$/iso-BuOH (6/4) mixture and extracted with a solution of 0.5 eq. of HCl. The acidic aqueous phase was extracted a second time with a mixture of CH$_2$Cl$_2$/iso-BuOH (6/4). The combined organic phases were first washed with a 5% (weight) aqueous solution of Na$_2$CO$_3$ containing 1.05 equivalents of sodium tetraphenylborate (TPBNa) (Mw=342 g,), and then 4 times with a 5% (weight) aqueous NaCl solution.

After the organic phase had been concentrated in vacuo, methoxyethanol was added in several portions to the concentrate to eliminate traces of iso-butanol. It was then further evaporated. The concentrate was then finally diluted with methoxyethanol and slowly added to a cold (0 to 5° C.) 5% (weight) aqueous NaCl solution. The peptide precipitated and was kept for at least 30 min at low temperature and then filtered.

The solid was washed 3 times with cold (0±5° C.) demineralised water. Thereafter, the solid was redissolved in MeOH and stirred until a slightly cloudy solution was obtained. The solution was partially concentrated and the methanolic solution was then added slowly to a cooled aqueous NaCl 5% (weight) solution. The precipitate was kept for at least 30 min at low temperature before it was filtered off. Finally the solid was washed 3 times with cold demineralised water (0° C.±5° C.) and dried under vacuum (45° C.). An off white solid was finally obtained. The yield based on the NMR measurement of the content was 89%.

Synthesis of HCl.H-Arg-Lys(Boc)-NH$_2$

A methanol solution of 1.00 equivalent of TPB.Z-Arg-Lys(Boc)-NH$_2$ (Mw=535.6; purity=62.0%) was passed several times through a column containing a methanol washed resin IRA 958 (Mw=1000; 3.00 equivalents). After checking the exchange by HPLC, the resin was filtered and washed three times with methanol. The combined organic phases were partially concentrated in vacuo. The concentrated solution was diluted with water.

Pd catalyst (Mw=106.4; 2% weight) were added and the suspension then hydrogenated for at least 5 hours at 35±5° C. The catalyst was filtered off, washed twice with a mixture methanol/water. The filtrate was evaporated in vacuo, the residue suspended in DMA and partially evaporated in vacuo in order to eliminate traces of water. After checking the water content, the final solution was titrated by HCl (0.1N) and further used without any purification.

Yield (based on the titration): 90%.

EXAMPLE 2

Synthesis of 2HCl.H-1-Trp-Arg-Arg-Lys(Boc)-NH$_2$(SEQ ID NO: 2)

Synthesis of Z-Trp-Arg-Arg-Lys(Boc)-NH$_2$.2TPB (SEQ ID NO: 2)

1.00 equivalent Z-Trp-Arg-OH (Mw=494.5; purity=85.0%,) and 1.10 equivalents HOOBt (Mw=163.13) were added to the DMA solution of 1.15 equivalents HCl.H-Arg-Lys(Boc)-NH$_2$ (Mw=437.5; purity=20.0%;) which had been previously diluted with CH$_2$Cl$_2$. After cooling the solution to −5±5° C., 1.00 equivalent HCl/dioxane 4N was slowly poured in and then 1.10 equivalents EDC (Mw=191.7) were added. The reaction mixture was stirred at −5±5° C. for at least 3 hours and then at least for 8 hours at 5±5° C. After checking the completion of the reaction by HPLC, the reaction mixture was diluted with a CH$_2$Cl$_2$/sec-butanol mixture (6/4), washed first with a 5% (weight) aqueous solution of NaCl containing HCl (0.5 eq.), then with 1900 ml of a 5% (weight) aqueous solution of Na$_2$CO$_3$ containing 2.2 equivalents NaTPB (,Mw=342), and finally five times with a 5% (weight) aqueous solution of NaCl. After the concentration of the organic layer, the residue was dissolved in methanol and then concentrated in vacuo in order to eliminate most of the remaining CH$_2$Cl$_2$. This final solution was titrated by NMR and further used without any purification.

Yield (based on titration content)=83%.

Synthesis of 2HCl.H-Trp-Arg-Arg-Lys(Boc)-NH$_2$(SEQ ID NO: 2)

The methanol solution of 1.00 equivalent of 2TPB.Z-Trp-Arg-Arg-Lys (Boc)-NH$_2$ (Mw=878.11) were passed several times through a column containing 6.00 equivalents of a methanol washed resin IRA 958 (Mw=1000). After checking the exchange by HPLC, the resin was filtered and washed three times with methanol. The combined organic phases were partially concentrated in vacuo. The concentrated solution was diluted with water and Pd catalyst were added. The suspension was then hydrogenated for at least 3 hours at 35±5° C. The catalyst was filtered off and washed twice with methanol. The filtrate was evaporated in vacuo, the residue dissolved in DMA and further concentrated in order to eliminate the remaining water. After the water content was checked, the precipitate was dissolved in DMA and partially evaporated in vacuo in order to adapt the weight of the solution. The final solution was titrated by 0.1N HCl and further used without any purification.

Yield (based on the titration): 95%.

EXAMPLE 3

Synthesis of 2HCl.H-Trp-Trp-Pro-Trp-Arg-Arg-Lys(Boc)-NH$_2$ (SEQ ID NO: 3)

Synthesis of Z-Trp-Trp-Pro-Trp-Arg-Arg-Lys(Boc)-NH$_2$.2TPB (SEQ ID NO: 3)

1.00 equivalent of Z-Trp-Trp-Pro-OH (Mw=621.7; purity=94.0%) was added to the DMA solution of 1.05 equivalents 2HCl.HTrp-Arg-Arg-Lys(Boc)-NH$_2$ (Mw=816.9; purity=15.0%) previously diluted with CH$_2$Cl$_2$. Then, 1.20 equivalents N,N'-Diisopropylethylamine (DIPEA) (Mw=129.2) and 1.05 equivalents of 2-(1H-benzotriazole-1-yl)-1,1,3,3-tetramethyluroniumhexafluorophosphate) (HBTU) (Mw=379.24) were added.

The reaction mixture was stirred at room temperature for at least 1 hour. After checking the completion of the reaction by HPLC, the reaction mixture was diluted with a CH$_2$Cl$_2$/iso-butanol mixture (8/2), washed first with a 5% (weight) aqueous solution of NaCl and HCl (1.5 eq.), then with a 5% (weight) aqueous solution of Na$_2$CO$_3$ and 2.2 equivalents NaTPB (Mw=342 g/mol), and finally three times with a 5% (weight) aqueous solution of NaCl. After concentration of the organic layer, the residual oil was several times dissolved in methoxyethanol, then concentrated in vacuo in order to eliminate most of the remaining iso-butanol. After GC control, the concentrate was precipitated by slowly pouring it into cold (0±5° C.) 5% (weight) aqueous solution of NaCl. After stirring for at least 1 hour, the suspension was filtered and washed twice with cold water. The precipitate was dried in vacuo at 45° C. A white solid was finally obtained.

Yield (based on NMR content)=98%.

Synthesis of 2HCl.H-Trp-Trp-Pro-Trp-Arg-Arg-Lys(Boc)-NH$_2$(SEQ ID NO: 3)

A methanol solution of 1.00 equivalent of 2TPB.Z-Trp-Trp-Pro-Trp-Arg-Arg-Lys(Boc)-NH$_2$ (SEQ ID NO: 3) (Mw=1347.5; purity=64.0%) was passed several times through a column containing a methanol washed resin IRA 958 (or Amberjet C1 1000; 6.00 equivalents). After checking the exchange by HPLC, the resin was filtered, washed three times. The combined organic phases were partially concentrated in vacuo and then diluted with water. Finally, 2% (weight) of Pd catalyst were added and the suspension hydrogenated for at least 3 hours at 40° C. The catalyst was filtered off, washed three times with a mixture of methanol/water. The combined filtrates were evaporated in vacuo, the residue suspended in DMA and further concentrated in order to eliminate the remaining water. After checking the water content, the solution was titrated by HCl (0.1 N), AgNO$_3$ (0.1N) or NMR and further used without any purification.

Yield (based on titration)=82%.

EXAMPLE 4

Synthesis of Z-Arg-Trp-Pro-Trp-Trp-Pro-Trp-Arg-Arg-Lys(Boc)-NH$_2$.3TPB (SEQ ID NO: 4)

1.00 equivalent of Z-Arg-Trp-Pro-OH (Mw=591.65; purity=96.0%), 1.00 equivalent of HCl/dioxane (4N;) and 1.05 equivalents HOBt (Mw=135.12; purity=98.0%) were added to 1.00 equivalent 2HCl.H-Trp-Trp-Pro-Trp-Arg-Arg-Lys(Boc)-NH$_2$ (SEQ ID NO: 3) (Mw=1213.4; purity=85.0%;) in solution in DMA diluted with CH$_2$Cl$_2$. After the solution had been cooled to 10±5° C., 1.02 equivalents EDC (Mw=191.7) were added. The reaction mixture was stirred at 10±5° C. for 30 min and then at least 4 hours at room temperature. After the completion of the reaction was confirmed by HPLC, the reaction mixture was diluted with a CH$_2$Cl$_2$/iso-butanol mixture (8/3), washed first with a 5% (weight) aqueous NaCl solution with HCl (0.5 eq.), then with a 5% (weight) aqueous solution of Na$_2$CO$_3$, containing 3 eq NaTPB (Mw=342), and finally twice with a 5% (weight) aqueous solution of NaCl. After concentration of the organic layer, the residual oil was several times dissolved in methoxyethanol, then concentrated in vacuo in order to eliminate most of the iso-butanol. After GC control, the concentrate was precipitated by slowly pouring it into cold 5% (weight) aqueous solution of NaCl. After stirring for at least 1 hour, the suspension was filtered, washed twice with cold water. The precipitate was dried at 40±5° C. An off white solid was finally obtained.

Yield (based on NMR content)=87%.

A methanol solution of 1.00 equivalent of 3TPB.Z-Arg-Trp-Pro-TrpTrp-Pro-Trp-Arg-Arg-Lys(Boc)-NH$_2$ (Mw=1787.1; purity=57.0%;) was passed several times through a column containing a methanol washed resin TRA 958 (Mw=1000, 9.00 equivalents). After the exchange had been checked by HPLC, the resin was filtered and washed three times with methanol. The combined organic phases were partially concentrated in vacuo. The concentrated solution was then diluted with water and Pd catalyst was added. The suspension was then hydrogenated for at least 6 hours at 35±5° C. The catalyst was filtered off, washed three times with a mixture methanol/water. The combined filtrates were evaporated in vacuo, the residue suspended in DMA and further concentrated in order to eliminate the remaining water. After checking the water content, the solution was titrated by HCl (0.1N) or NMR and further used without any purification.

Yield (based on NMR content measurement): 93%.

EXAMPLE 5

Synthesis of Z-(D)Arg-Gly-Arg-pNA.2HCl

Synthesis of Z-(D)Arg-Gly-Arg-pNA.2HCl 7.7 g of Z-(D)ArgOH (25 mmoles) and 13.8 g of 2HCl.H-Gly-ArgpNA were dispersed in about 100 ml of DMA at room temperature till complete dissolution. The mixture was then cooled to 0° C. and DIPEA (N,N'-diisopropyl ethyl amine) was added to neutralize the excess of HCl, followed by 3.6 g of HOBt (26.13 mmoles) and 5.7 g of DCC (27.5 mmoles). The solution was left to stir at least 1 hour at 0° C. before being conditioned to 25±5° C. When the reaction was considered as completed (followed by HPLC), the crude was concentrated in vacuo, and the concentrate was then diluted with water to precipitate the DCU which was then removed by filtration and washed with water. The aqueous solution was washed several times with DCM to remove DMA (dimethyl acetamide) and HOBt. Two equivalents of TPBNa and 500 ml of DCM were poured into the aqueous solution while the pH was adjusted between 6.5 and 7.5 by the controlled addition of an aqueous NaHCO3 solution. After 1 hour of mixing, the aqueous phase was discarded and the organic phase was washed several times with an aqueous solution of NaCl and finally with water. The solvent was removed under vacuum and replaced with MeOH.

Isolation of Z-(D)Arg-Gly-Arg-pNA.2TPB,

The methanolic solution of Z-(D)Arg-Gly-Arg-pNA.2TPB was then poured into an aqueous 5% solution of NaCl at 0±5° C. to precipitate Z-(D)Arg-Gly-Arg-pNA.2TPB. After filtration, washing by water and drying under vacuum, Z-(D)Arg-Gly-Arg-pNA.2TPB was obtained as a white solid.

Isolation of the Bischlorhydrate Salt of Z-(D)Arg-Gly-Arg-pNA

The TPB salt was dissolved in methanol and the solution was passed several times through a column containing a methanol washed resin IRA 958. After checking the exchange by HPLC, the resin was washed several times with methanol. The combined concentrated filtrates were concentrated under vacuum and the solid obtained was purified by HPLC and finally lyophilized to yield Z-(D)Arg-Gly-Arg-pNA as its bischlorhydrate salt.

EXAMPLE 6

Synthesis of Ac-(D)Arg-Gly-Arg-pNA.2HCl

Isolation of Purified Ac-(D)Arg-Gly-Arg-pNA.2TPB,

The pH of a Ac-(D)Arg-Gly-Arp-pNA.2TFA solution in water/acetonitrile (31 l) was adjusted to 7±0.5 by adding an aqueous solution of NaHCO$_3$. The acetonitrile fraction was evaporated in vacuo (the volume of the solution was maintained by adding water if necessary). 1 kg TPBNa and 1.1 kg NaHCO$_3$ were dissolved in about 20 l water. The concentrated peptide solution was then gradually poured into the aqueous solution TPBNa/NaHCO$_3$. The Ac-(D)Arg-Gly-Arg-pNA.2TPB precipitated. After filtration, washing by water (40 l) and drying under vacuum (45° C.), 1.6 kg of Ac-(D)Arg-Gly-Arg-pNA.2TPB were obtained.

Isolation of the Purified Ac-(D)Arg-Gly-Arg-pNA.2HCl,

The TPB salt was dissolved in 20 l methanol which was passed several times through a column containing a methanol washed resin IRA 958 (7.6 kg resin). After checking the exchange by HPLC, the resin was washed several times with methanol (11 l each time). The combined concentrated filtrates were precipitated in 44 l cooled (−5°±5° C.) acetonitrile. After washing with acetonitrile (12 l), drying under vacuum, the precipitate gave 0.8 kg of off white solid. If necessary, the Ac-(D)Arg-Gly-Arg-pNA.2HCl can be precipitated a second time.

EXAMPLE 7

Synthesis of Mpr(*)-Har-Gly-Asp(OtBu)-Trp-Pro-Cys(*)-NH$_2$ (SEQ ID NO: 5)

(*) indicates a disulfide bridge between the mercaptopropionic acid and the cysteinamid.

550 ml of a methanol solution of 46.6 g of Mpr(Trt)-Har-Gly-Asp(OtBu)-Trp-Pro-Cys (Trt)-NH$_2$ (SEQ ID NO: 5)

(Mw=1374.8 g/mol, 20 mmol=1.00 equivalent) was treated with 130 g of a washed resin IRA 958 (Mw=1000 g/mol; 6.72 equivalents). After checking the exchange by HPLC, the resin was filtered and washed several times with 340 ml methanol. The combined organic phases were diluted by adding 1500 ml methanol, 5400 ml dichloromethane and finally 180 ml water. 24 g of iodine was added to the diluted solution. After checking the cyclisation by HPLC, the remaining iodine is quenched by adding 700 ml of $Na_2S_2O_3$ (3.6% weight) in aqueous solution. The reaction mixture was then neutralized by 190 ml of resin acetate (Mw=720 g/mol; 57 equivalents). After filtration and washing of the resin by 210 ml methanol and 1800 ml water, the organic layer was separated from the aqueous one. The peptide (SEQ ID NO: 5) was extracted with 21 g of NaTPB (Mw=342.2 g/mol; 3 equivalents) from the neutralized aqueous layer by adding 10000 ml dichloromethane. After separation and evaporation of the organic layer, the residue was dissolved in methanol (900 ml) and then concentrated in vacuo in order to eliminate most of the remaining dichloromethane. The methanol solution was suspended into 2400 g of a washed resin IRA 958 (Mw=1000 g/mol; 12.1 equivalents). After checking the exchange by HPLC and washing the resin, the combined organic phases were diluted by adding 240 ml of acetic acid. This solution was further purified by preparative HPLC.

EXAMPLE 8

Storage of Mpr(Trt)-Har-Gly-Asp(OtBu)-Trp-Pro-Cys(Trt)-$NH_2$ TPB Salt (SEQ ID NO: 5)

Solid Mpr(Trt)-Har-Gly-Asp(OtBu)-Trp-Pro-Cys(Trt)-$NH_2$ TPB salt (SEQ ID NO: 5) was obtained by precipitation in accordance with the process according to the invention. The product was stored for more than 1 year at a temperature of 20-25° C. The solid TPB salt had remained substantially stable after the storage.

```
                    SEQUENCE LISTING

<110>   SOLVAY SA

<120>   Use of a TPB salt for the separation of biomolecules

<130>   S200918

<160>   5

<170>   PatentIn version 3.3

<210>   1

<211>   12

<212>   PRT

<213>   Artificial

<220>

<223>   Synthetic peptide

<400>   1

Ile Leu Arg Trp Pro Trp Trp Pro Trp Arg Arg Lys
1               5                   10

<210>   2

<211>   4

<212>   PRT

<213>   Artificial

<220>

<223>   Synthetic Peptide

<400>   2

Trp Arg Arg Lys
1

<210>   3

<211>   7

<212>   PRT

<213>   Artificial
```

SEQUENCE LISTING

```
<220>
<223>   Synthetic Peptide
<400>   3
Trp Trp Pro Trp Arg Arg Lys
1               5

<210>   4
<211>   10
<212>   PRT
<213>   Artificial
<220>
<223>   Synthetic Peptide
<400>   4
Arg Trp Pro Trp Trp Pro Trp Arg Arg Lys
1               5                   10

<210>   5
<211>   7
<212>   PRT
<213>   Artificial
<220>
<223>   Synthetic Peptide
<220>
<221>   MISC_FEATURE
<222>   (1)...(1)
<223>   Mercaptopropionic acid
<220>
<221>   MISC_FEATURE
<222>   (2)...(2)
<223>   Homoarginine
<400>   5
Xaa Xaa Gly Asp Trp Pro Cys
1               5
```

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial
<220> FEATURE:
<223> OTHER INFORMATION: Synthetic peptide
```

```
<400> SEQUENCE: 1

Ile Leu Arg Trp Pro Trp Trp Pro Trp Arg Arg Lys
1               5                   10

<210> SEQ ID NO 2
<211> LENGTH: 4
<212> TYPE: PRT
<213> ORGANISM: Artificial
<220> FEATURE:
<223> OTHER INFORMATION: Synthetic Peptide

<400> SEQUENCE: 2

Trp Arg Arg Lys
1

<210> SEQ ID NO 3
<211> LENGTH: 7
<212> TYPE: PRT
<213> ORGANISM: Artificial
<220> FEATURE:
<223> OTHER INFORMATION: Synthetic Peptide

<400> SEQUENCE: 3

Trp Trp Pro Trp Arg Arg Lys
1               5

<210> SEQ ID NO 4
<211> LENGTH: 10
<212> TYPE: PRT
<213> ORGANISM: Artificial
<220> FEATURE:
<223> OTHER INFORMATION: Synthetic Peptide

<400> SEQUENCE: 4

Arg Trp Pro Trp Trp Pro Trp Arg Arg Lys
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Mercaptopropionic acid
<220> FEATURE:
<221> NAME/KEY: MISC_FEATURE
<222> LOCATION: (2)..(2)
<223> OTHER INFORMATION: Homoarginine

<400> SEQUENCE: 5

Xaa Xaa Gly Asp Trp Pro Cys
1               5
```

The invention claimed is:

1. A process for the separation of a biomolecule from a liquid medium, wherein the biomolecule:
   i) is selected from the group consisting of a peptide, a peptide derivative, and combinations thereof; and
   ii) comprises between 1 and 20 cationic group(s), wherein at least one cationic group is a guanidine group;
   and wherein the process comprises the steps of:
   a) providing a first organic solution containing the biomolecule; and
   b) adding a tetraphenylborate (TPB) salt together with an alkaline agent to the first organic solution to form a biomolecule-TPB salt in the first organic solution,
   c) concentrating the first organic solution containing the biomolecule-TPB salt,
   wherein the process further comprises the step of performing a synthesis step without isolation of the biomolecule-TPB salt, wherein said synthesis step comprises coupling, deprotection, and purification.

2. The process of claim 1 comprising the preliminary step of washing the first organic solution containing the biomolecule with an aqueous solution before the addition of the tetraphenylborate salt.

3. The process of claim 1, further comprising the step of washing the first organic solution or the concentrated organic solution containing the biomolecule-TPB salt with an aqueous solution after the addition of tetraphenylborate salt.

4. The process of claim 1, wherein the tetraphenylborate salt is NaTPB.

5. The process of claim 1, wherein the at least one cationic group is an amino group or a guanidine group.

6. The process of claim 1, wherein the alkaline agent is an inorganic base.

7. The process of claim 1, wherein the first organic solution comprises an organic solvent is selected from the group consisting of halocarbons, esters, ethers and combinations thereof.

8. A process for the separation of a biomolecule from a liquid medium, wherein the biomolecule:
   i) is selected from the group consisting of a peptide, a peptide derivative, and combinations thereof; and
   ii) comprises between 1 and 20 cationic group(s), wherein at least one cationic group is a guanidine group;

and wherein the process comprises the steps of:
   a) providing a first organic solution containing the biomolecule; and
   b) adding a tetraphenylborate (TPB) salt together with an alkaline agent to the first organic solution to form a biomolecule-TPB salt in the first organic solution,
   c) concentrating the first organic solution containing the biomolecule-TPB salt; adding to the concentrated organic solution containing the biomolecule-TPB salt an organic solvent selected from the group consisting of alcohols, amide-type solvents, halocarbons, esters, ethers, and combinations thereof, to form a second organic solution containing the biomolecule-TPB salt, wherein said process further comprises the step of performing a synthesis step without isolation of the biomolecule-TPB salt, wherein the synthesis step comprises coupling, deprotection, and purification.

9. The process of claim 8, wherein the alkaline agent is an inorganic base.

10. The process of claim 8, wherein the first organic solution comprises an organic solvent selected from the group consisting of halocarbons, esters, ethers and combinations thereof.

11. The process according to claim 8, wherein the biomolecule is precipitated or crystallized as a solid biomolecule-TPB salt from the second organic solution.

* * * * *